US010918307B2

(12) United States Patent
Olson et al.

(10) Patent No.: US 10,918,307 B2
(45) Date of Patent: Feb. 16, 2021

(54) CATHETER NAVIGATION USING IMPEDANCE AND MAGNETIC FIELD MEASUREMENTS

(75) Inventors: Eric S. Olson, Maplewood, MN (US); Carlos Carbonera, St. Paul, MN (US); Lev A. Koyrakh, Plymouth, MN (US); Daniel R. Starks, Lake Elmo, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 761 days.

(21) Appl. No.: 13/231,284

(22) Filed: Sep. 13, 2011

(65) Prior Publication Data

US 2013/0066193 A1    Mar. 14, 2013

(51) Int. Cl.
*A61B 5/00* (2006.01)
*A61B 5/06* (2006.01)
(Continued)

(52) U.S. Cl.
CPC ............ *A61B 5/063* (2013.01); *A61B 5/062* (2013.01); *A61B 34/20* (2016.02); *A61B 5/0538* (2013.01);
(Continued)

(58) Field of Classification Search
CPC ......... A61B 5/063; A61B 34/20; A61B 5/062; A61B 2034/2051; A61B 2034/2053;
(Continued)

(56) References Cited

U.S. PATENT DOCUMENTS

| 5,297,549 A | 3/1994 | Beatty |
| 5,391,199 A | 2/1995 | Ben-Haim |

(Continued)

FOREIGN PATENT DOCUMENTS

| CN | 101782358 | 7/2010 |
| CN | 103298516 | 9/2013 |

(Continued)

OTHER PUBLICATIONS

Collins English Dictionary—Complete and Unabridged 10th Edition, 2009, Harper Collins Publishers.*

(Continued)

*Primary Examiner* — Joanne M Hoffman
(74) *Attorney, Agent, or Firm* — Dykema Gossett PLLC

(57) ABSTRACT

A method of operating a positioning system by registering a first coordinate system of a first positioning system in a second coordinate system of a second positioning system includes determining an interpolation function configured to register the first, non-orthonormal coordinate system in the second, orthonormal coordinate system. Fiducial pairs are collected by the respective positioning systems, each of which contain a respective coordinate in the respective coordinate system, both of which refer to the same physical point in three dimensional space. Establishing a working interpolation function involves an analysis of the fiducial pairs using a thin-plate spline algorithm. The method further includes repeatedly obtaining a first coordinate in the first coordinate system and determining a corresponding second coordinate in the second coordinate system in accordance with the interpolation function.

11 Claims, 6 Drawing Sheets

(51) Int. Cl.
  *A61B 34/20* (2016.01)
  *A61B 5/0538* (2021.01)
  *A61B 90/00* (2016.01)

(52) U.S. Cl.
  CPC ........... *A61B 5/6852* (2013.01); *A61B 5/7207* (2013.01); *A61B 2034/2051* (2016.02); *A61B 2034/2053* (2016.02); *A61B 2090/0818* (2016.02)

(58) Field of Classification Search
  CPC .......... A61B 2090/0818; A61B 5/7207; A61B 5/6852; A61B 5/0538
  USPC ....................................................... 600/424
  See application file for complete search history.

(56) References Cited

U.S. PATENT DOCUMENTS

| | | | |
|---|---|---|---|
| 5,443,489 A | 8/1995 | Ben-Haim | |
| 5,480,422 A | 1/1996 | Ben-Haim | |
| 5,546,951 A | 8/1996 | Ben-Haim | |
| 5,568,809 A | 10/1996 | Ben-haim | |
| 5,662,108 A | 9/1997 | Budd | |
| 5,694,945 A | 12/1997 | Ben-Haim | |
| 5,697,337 A | 12/1997 | Takahashi et al. | |
| 5,697,377 A | 12/1997 | Wittkampf | |
| 5,718,241 A | 2/1998 | Ben-Haim | |
| 5,738,096 A | 4/1998 | Ben-Haim | |
| 5,840,025 A | 11/1998 | Ben-Haim | |
| 5,944,022 A | 8/1999 | Nardella | |
| 5,954,665 A | 9/1999 | Ben-Haim | |
| 5,983,126 A | 11/1999 | Wittkampf | |
| 6,016,439 A | 1/2000 | Acker | |
| 6,063,022 A | 5/2000 | Ben-Haim | |
| 6,066,094 A | 5/2000 | Ben-Haim | |
| 6,226,542 B1 | 5/2001 | Reisfeld | |
| 6,233,476 B1 | 5/2001 | Strommer et al. | |
| 6,288,785 B1 | 9/2001 | Frantz et al. | |
| 6,301,496 B1 | 10/2001 | Reisfeld | |
| 6,484,118 B1* | 11/2002 | Govari .................. A61B 5/06 |  |
| | | | 702/150 |
| 6,640,119 B1 | 10/2003 | Budd | |
| 6,728,562 B1 | 4/2004 | Budd | |
| 6,939,309 B1 | 9/2005 | Beatty | |
| 6,947,785 B1 | 9/2005 | Beatty | |
| 6,978,168 B2 | 12/2005 | Beatty | |
| 6,990,370 B1 | 1/2006 | Beatty | |
| 7,072,707 B2* | 7/2006 | Galloway et al. ............ 600/424 | |
| 7,088,099 B2* | 8/2006 | Doddrell et al. ............. 324/309 | |
| 7,187,810 B2* | 3/2007 | Clune ................ A61B 1/00009 | |
| | | | 382/128 |
| 7,197,354 B2 | 3/2007 | Sobe et al. | |
| 7,263,397 B2 | 8/2007 | Hauck et al. | |
| 7,379,769 B2* | 5/2008 | Piron et al. ................... 600/415 | |
| 7,386,339 B2 | 6/2008 | Strommer et al. | |
| 7,536,218 B2 | 5/2009 | Govari et al. | |
| 7,583,275 B2 | 9/2009 | Neumann | |
| 7,672,504 B2 | 3/2010 | Childers | |
| 7,747,305 B2* | 6/2010 | Dean et al. .................... 600/407 | |
| 8,111,059 B1 | 2/2012 | King et al. | |
| 8,326,419 B2 | 12/2012 | Rosenberg et al. | |
| 8,473,216 B2 | 6/2013 | Sun et al. | |
| 8,569,706 B2 | 10/2013 | Thiruvenkadam et al. | |
| 9,271,664 B2 | 3/2016 | Wedan et al. | |
| 2003/0093004 A1 | 5/2003 | Sosa et al. | |
| 2003/0135120 A1* | 7/2003 | Parks .................... A61B 5/037 | |
| | | | 600/463 |
| 2004/0097806 A1 | 5/2004 | Hunter | |
| 2004/0254437 A1 | 12/2004 | Hauck | |
| 2005/0057246 A1* | 3/2005 | Orozco ............... G01R 31/311 | |
| | | | 324/228 |
| 2005/0137478 A1 | 6/2005 | Younge | |
| 2005/0222554 A1 | 10/2005 | Wallace | |
| 2005/0288577 A1 | 12/2005 | Weese | |
| 2006/0084867 A1 | 4/2006 | Tremblay | |
| 2006/0095022 A1 | 5/2006 | Moll | |
| 2006/0100610 A1 | 5/2006 | Wallace | |
| 2007/0016007 A1* | 1/2007 | Govari et al. ................ 600/424 | |
| 2007/0055331 A1 | 3/2007 | Merfeld | |
| 2007/0060833 A1 | 3/2007 | Hauck et al. | |
| 2007/0110665 A1 | 5/2007 | Bolan et al. | |
| 2007/0181139 A1 | 8/2007 | Hauck | |
| 2008/0161681 A1 | 7/2008 | Hauck et al. | |
| 2008/0221425 A1 | 9/2008 | Olson et al. | |
| 2008/0221643 A1 | 9/2008 | Olson et al. | |
| 2009/0028416 A1 | 1/2009 | Floeder | |
| 2009/0067755 A1* | 3/2009 | Khamene et al. ............ 382/300 | |
| 2009/0161827 A1 | 6/2009 | Gertner | |
| 2009/0198126 A1* | 8/2009 | Klingenbeck-Regn ....... 600/426 | |
| 2010/0079158 A1 | 4/2010 | Bar-Tal et al. | |
| 2010/0099981 A1 | 4/2010 | Fishel | |
| 2010/0149183 A1* | 6/2010 | Loewke ............. G06K 9/00134 | |
| | | | 345/424 |
| 2010/0152571 A1* | 6/2010 | Hartmann ............. G01S 5/0263 | |
| | | | 600/424 |
| 2010/0268059 A1 | 10/2010 | Ryu | |
| 2010/0298826 A1 | 11/2010 | Leo et al. | |
| 2011/0058239 A1 | 3/2011 | Lundvall et al. | |
| 2011/0062344 A1 | 3/2011 | Kornblau | |
| 2011/0158488 A1 | 6/2011 | Cohen et al. | |
| 2011/0160569 A1 | 6/2011 | Cohen | |
| 2011/0160593 A1 | 6/2011 | Deno et al. | |
| 2011/0166407 A1 | 7/2011 | Sumanaweera et al. | |
| 2011/0172927 A1 | 7/2011 | Sahasrabudhe et al. | |
| 2011/0267340 A1* | 11/2011 | Kraus et al. .................. 345/419 | |
| 2011/0282473 A1* | 11/2011 | Pavlovskaia ............ G06F 19/00 | |
| | | | 700/98 |
| 2012/0165658 A1 | 6/2012 | Shi et al. | |
| 2012/0172702 A1 | 7/2012 | Koyrakh | |
| 2012/0172724 A1 | 7/2012 | Hill et al. | |
| 2012/0265054 A1 | 10/2012 | Olson | |
| 2012/0302869 A1* | 11/2012 | Koyrakh ................ A61B 5/062 | |
| | | | 600/409 |

FOREIGN PATENT DOCUMENTS

| | | |
|---|---|---|
| EP | 1743575 | 1/2007 |
| EP | 2168478 | 3/2010 |
| JP | 2006072933 | 3/2005 |
| JP | 2007021218 A | 2/2007 |
| JP | 2010520780 A | 6/2010 |
| WO | 1994/004938 | 3/1994 |
| WO | 1996/005768 | 2/1996 |
| WO | 1998/040026 | 9/1998 |
| WO | 2001/006917 | 2/2001 |
| WO | WO-2008-083111 A | 7/2008 |
| WO | 2008/112039 | 9/2008 |
| WO | 2008/112420 | 9/2008 |

OTHER PUBLICATIONS

G Roussos, BJC Baxter, "Rapid evaluation of radial basis functions", 2005, Journal of Computational and Applied Mathematics, vol. 180, pp. 51-70.*
http://www1.cs.columbia.edu/~allen/PHOTOPAPERS/hmwk1.pdf, downloaded Aug. 15, 2017.*
Wittkampf, Fred H. M., et al., "LocaLisa: New Technique for Real-Time 3-Dimensional Localization of Regular Intracardiac Electrodes", Circulation, vol. 99, 1312-1317, 1999.
Bennink, H.E., et al., "Warping a Neuro-Anatomy Atlas on 3D MRI Data with Radial Basis Functions", IFMBE Proceedings, vol. 15, Part 2, 28-32, 2007.
Bookstein, F.L., "Principal warps: Thin-Plate Splines and the Decomposition of Deformations", IEEE Trans. Pattern Analysis and Machine Intelligence, vol. 11(6), 567-585, Jun. 1989.
Donato, G. and Belongie, S., "Approximate Thin Plate Spline Mappings", EeeV, 21-31, 2002.
Reinsch, C., "Smoothing by Spline Functions", Numerische Mathematik, vol. 10, 177-183, 1967.
Masson, L., et al., "Tracking 3D Objects using Flexible Models", BMVC, 2005.

(56) References Cited

OTHER PUBLICATIONS

Carr, J.C., et al., "Reconstruction and Representation of 3D Objects with Radial Basis Functions", Siggraph '01 proceedings of the 28th annual conference on Computer graphics and interactive techniques, 2001.

Chui, H. and Rangaranjan, A., "A new point matching algorithm for non-rigid registration", eVIU, 2003.

"International Search Report & Written Opinion", PCT/US2012/030925 dated Jun. 20, 2012.

Title: International Search Report & Written Opinion Citation: PCT/US2012/022678 Publication Date: May 30, 2012.

Title: International Search Report and Written Opinion Citation: PCT/US2008/054969 Publication Date: Aug. 15, 2006.

Bookstein, Fred L.; "Thin-Plate splines and the atlas problem for biomedical images"; Lecture Notes in Computer Science, vol. 511/1991 Reference Pages: Abstract Publication Date: 1991.

Bors, Adrian G.; "Median Radial Basis Functions Neural Network"; Citation: IEEE Computational Intelligence Society, vol. 7, Issue 6 Reference pp. 1-33 Publication Date: 1996.

Chui, Haili, "A new algorithm for non-rigid point matching"; IEEE Conference on Computer Vision and pattern, vol. 2; Reference pp. 44-51; Publication Date: 2000.

Ebeling, H., "ASMOOTH: A simple and efficient algorithm for adaptive kernel smoothing of two-dimensional imaging data"; Mon. Not. R. Astron. Soc., vol. 368; Reference pp. 65-73; Publication Date: 2006.

Jain, Ameet Kumar; "FTRAC—a robust fluoroscope tracking fiducial"; Medical Physics, vol. 32, No. 10; Reference pp. 3185-3198; Publication Date: Oct. 2005.

Ju, Tao; "Mean Value Coordinates for Closed Triangular Meshes", ACM Transactions on Graphics 24(3); Reference pp. 561-566; Publication Date: Jul. 2005.

Orr, Mark J; "Introduction to radial basis function networks"; Reference pp. 1-67; Publication Date: 1996.

Park, J.; "Universal approximation using radial-basis-function networks"; Neural Computation, vol. 3, No. 2; Reference Pages: Abstract; Publication Date: 1991.

Wiley, David F.; "Evolutionary Morphing"; Proceedings of IEEE Visualization; Reference pp. 431-438; Publication Date: 2005.

Kabra, Rajesh et al.,"Recent trends in imaging for atrial fibrillation ablation", Indian Pacing and Electrophysiology Journal, pp. 215-227, May 5, 2010.

International Search Report and Written Opinion in PCT Application No. PCT/US2013/045885 (dated Oct. 1, 2013).

\* cited by examiner

CATHETER NAVIGATION USING IMPEDANCE AND MAGNETIC FIELD MEASUREMENTS

BACKGROUND OF THE INVENTION a. Field of the Invention

The instant invention relates generally to medical device navigation and more particularly to a system and method for registering a first medical device navigation system coordinate system with a second medical device navigation system coordinate system.

b. Background Art

Various systems are known for determining the position and orientation (P&O) of a medical device in a human body, for example, for visualization and navigation purposes. One such system is known as an electrical impedance-based positioning system. Electrical impedance-based systems generally include one or more pairs of body surface electrodes (e.g., patches) outside a patient's body, a reference sensor (e.g., another patch) attached to the patient's body, and one or more sensors (e.g., electrodes) attached to the medical device. The pairs can be adjacent, linearly arranged, or associated with respective axes of a coordinate system for such a positioning system. The system can determine P&O by applying a current across pairs of electrodes, measuring respective voltages induced at the device electrodes (i.e., with respect to the reference sensor), and then processing the measured voltages.

Another system is known as a magnetic field-based positioning system. This type of system generally includes one or more magnetic field generators attached to or placed near the patient bed or other component of the operating environment and one or more magnetic field detection coils coupled with a medical device. Alternatively, the field generators may be coupled with a medical device, and the detection coils may be attached to or placed near a component of the operating environment. The generators provide a controlled low-strength AC magnetic field in the area of interest (i.e., an anatomical region). The detection coils produce a respective signal indicative of one or more characteristics of the sensed field. The system then processes these signals to produce one or more P&O readings associated with the coils (and thus with the medical device). The P&O readings are typically taken with respect to the field generators, and thus the field generators serve as the de facto "origin" of the coordinate system of a magnetic field-based positioning system. Unlike an electrical impedance-based system, where the coordinate system is relative to the patient on which the body surface electrodes are applied, a magnetic field-based system has a coordinate system that is independent of the patient.

Both electrical impedance-based and magnetic field-based positioning systems provide advantages. For example, electrical impedance-based systems provide the ability to simultaneously locate (i.e., provide a P&O reading for) a relatively large number of sensors on multiple medical devices. However, because electrical impedance-based systems employ electrical current flow in the human body, the coordinate systems can be non-homogenous, anisotropic, and not orthonormal (i.e., the basic vectors of the coordinate system are not guaranteed to be at right angles to one another or to have proper unit lengths). Additionally, electrical impedance-based systems may be subject to electrical interference. As a result, geometries and representations that are rendered based on position measurements may appear distorted relative to actual images of subject regions of interest.

Magnetic field-based coordinate systems, on the other hand, are not dependent on characteristics of the patient's anatomy and provide a generally orthonormal coordinate system. However, magnetic field-based positioning systems are generally limited to tracking relatively fewer sensors.

There is therefore a need for a positioning system that minimizes or eliminates one or more of the challenges described above.

BRIEF SUMMARY OF THE INVENTION

It is desirable to provide a system that combines the advantages of an electrical impedance-based positioning system (e.g., positioning multiple sensors on multiple catheters) with the advantages of a magnetic-field based coordinate system (e.g., independence from patient anatomy, orthonormality). In an embodiment, such a system may be provided by registering the coordinate system of an electrical impedance-based positioning system in the coordinate system of a magnetic field-based positioning system. After registration, the electrical impedance-based positioning system can be operated in the coordinate system of the magnetic field-based positioning system.

A method of operating a positioning system includes a number of steps. The first step involves determining an interpolation function, which is configured to register a first, non-orthonormal coordinate system in a second, orthonormal coordinate system. This first step may be preliminary in nature (i.e., performed prior to a medical or mapping procedure). The method further includes the steps of obtaining a first coordinate in the first coordinate system and determining a corresponding second coordinate in the second coordinate system in accordance with the interpolation function. In an embodiment, these steps may be repeated in a real-time fashion, for example, during a medical procedure. Through the foregoing, coordinates obtained in an impedance-based positioning system, for example, may, in substantially real time, be presented as corresponding coordinates in a magnetic field-based coordinate system. The resulting coordinates may be used for several purposes in addition to tracking devices, such as collection of data points on or near a tissue surface for generating a geometrical shell. Such a shell may be more accurate than a shell based on coordinates in an electrical impedance-based coordinate system. The method thus relaxes the limitations on the number of sensors/devices that can be tracked, but includes the accuracy advantages of a patient-independent, orthonormal coordinate system.

In an embodiment, the step of determining the interpolation function may in turn include a number of sub-steps. The first sub-step involves collecting a plurality of fiducial pairs in three-dimensional (3D) space, each fiducial pair including (1) a first coordinate in the first coordinate system measured by a first positioning system and (2) a second coordinate in the second coordinate system measured by a second positioning system. Each coordinate in a fiducial pair corresponds to the same physical point in 3D space. The second sub-step involves applying a thin-plate spline algorithm to the plurality of fiducial pairs to yield the interpolation function.

A system for determining the position of a medical device comprises an electronic control unit (ECU), a computer-readable memory coupled to the ECU, and logic stored in the memory configured to be executed by the ECU. The logic is configured to determine an interpolation function and apply the interpolation function to a first coordinate in a first non-orthonormal coordinate system to determine a corresponding second coordinate in a second orthonormal coordinate system. In an embodiment, the logic may be configured to determine the interpolation function by applying a thin-plate spline algorithm to a plurality of fiducial pairs to yield the interpolation function. Each fiducial pair may include (1) a first coordinate in the first coordinate system measured by a first positioning system and (2) a second coordinate in the second coordinate system measured by a second positioning system. Significantly, each coordinate in the fiducial pair corresponds to the same physical point in 3D space. As with the method, in an embodiment, the logic may be configured to determine the interpolation function during a preliminary phase before, for example, a medical procedure. Thereafter, the logic operates to apply the now-defined interpolation function during the medical procedure.

DETAILED DESCRIPTION OF THE INVENTION

The following detailed description includes four parts. First, a system for operating a first (e.g., electrical-impedance based) medical positioning system (MPS) together with a second (e.g., magnetic field-based) MPS will be described generally. Second, an exemplary electrical impedance-based MPS will be described in greater detail. Third, exemplary embodiments of a magnetic field-based MPS will be described in greater detail. Finally, a method for operating a first (e.g., electrical impedance-based) MPS in the coordinate system of a second (e.g., magnetic field-based) MPS will be described.

Figure 1:
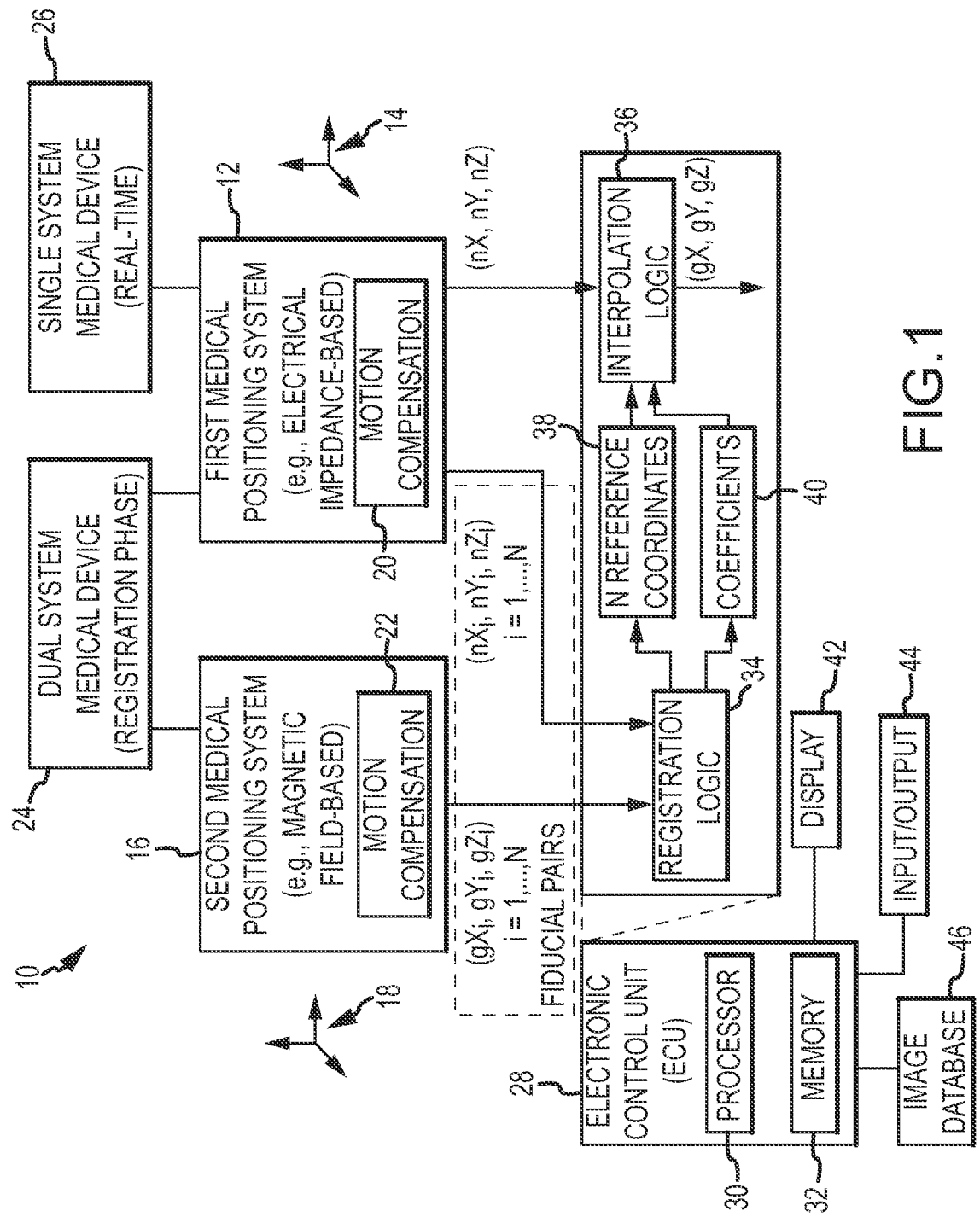
FIG. 1 is a block diagram view of a system for determining the position of a medical device by operating a first (e.g., electrical impedance-based) medical positioning system (MPS) together with a second (e.g., magnetic field-based) MPS.

System for Operating a First MPS With a Second MPS. Referring now to the drawings wherein like reference numerals are used to identify identical components in the various views, FIG. 1 is a block diagram of a system 10 for determining the position of a medical device by operating a first medical positioning system (MPS) (e.g., electrical-impedance based) together with a second MPS (e.g., magnetic field-based). As described in the Background, each type of positioning system has certain advantages and disadvantages. System 10 is configured to retain the advantages of both systems while overcoming the respective disadvantages.

System 10 shows a first MPS 12 (electrical impedance-based) and associated first coordinate system 14, a second MPS 16 (magnetic field-based) and associated second coordinate system 18, respective motion compensation blocks 20, 22, a dual-system medical device 24, a single-system medical device 26, an electronic control unit 28 (including associated processor 30 and memory 32), logic blocks and data structures including a registration block 34, an interpolation block 36, a reference coordinate data structure 38, a computed coefficient data structure 40, a display 42, an input/output interface 44 and an image database 46.

It should be understood that while ECU 28, MPS 12, and MPS 16 are shown separately, this is for ease of description purposes only and is not limiting in nature. In an embodiment, ECU 28, MPS 12, and MPS 16 may all be implemented in a single processing apparatus or distributed among multiple apparatus differently than as shown. For example, MPS 12 and MPS 16 may be combined in a single MPS separate from ECU 28. In a further embodiment, MPS 12 and MPS 16 may share components, such as ECG leads, for example. Other variations are possible, as understood by those of ordinary skill in the art.

MPS 12 may be an electrical impedance-based positioning system and is configured to acquire positioning (localization) data (i.e., position and orientation—P&O) associated with one or more electrodes attached to one or more medical devices in the body of a patient. As described in greater detail below in connection with FIGS. 2-3, system 12 may be coupled to one or more compatible medical devices (e.g., catheter, introducer, reference device, etc.) bearing one or more electrodes. Furthermore, the system 12 typically employs a plurality of body surface electrodes (i.e., patches). System 12, in an embodiment, applies excitation signals to patch pairs and measures resulting signals on the electrodes (and on the patches), which measured signals are analyzed by system 12 to produce output P&O readings. As shown, an exemplary position portion of a P&O reading may be expressed in three dimensions, for example, as a 3D coordinate (nX, nY, nZ). Depending on the configuration, a companion set of orientation values may also be determined. Due to a variety of factors, the associated coordinate system 14 may be non-homogenous, non-orthonormal, and anisotropic.

MPS 16 may be a magnetic field-based positioning system and is likewise configured to acquire positioning (localization) data (i.e., position and orientation—P&O) associated with one or more sensors attached or otherwise associated with one or more medical devices in the body of the patient. As described in greater detail below in connection with FIG. 5, MPS 16 may be coupled to one or more compatible medical devices bearing one or more sensors (e.g., field sensors, such as coils), and further, typically includes a plurality of electromagnetic field generators. MPS 16 controls both the electromagnetic field generation, as well as the detection of signals at each of the sensors, which detected signals are indicative of one or more field characteristics of the sensed fields. MPS 16 is configured to process the detected signals and output P&O readings. As shown, an exemplary position portion of a P&O reading may be expressed in three dimensions, for example, as a 3D coordinate (gX, gY, gZ). Depending on the configuration, a companion set of orientation values may also be determined. In general, the associated coordinate system 18 is homogeneous and orthonormal. However, as described in the Background, MPS 16 may be limited in the number of sensors for which P&O can be determined at one time.

It should be understood that coordinate systems 14, 18 may be independent of each other, with separate orientations and different origins, and may be movable relative to each other. In addition, in certain embodiments, motion compensation functionality may be provided by either or both of MPS 12 and MPS 16. In the illustrative embodiment, both positioning systems include such functionality, shown by motion compensation blocks 20, 22. Motion compensation functionality provided by blocks 20, 22 may be independent of each other. Generally, motion compensation blocks may allow for adjustment of raw position data obtained by MPS 12 and MPS 16, respectively, to account for movement of a patient body region of interest (ROI) relative to a pre-acquired image, series of images, or geometry of the ROI. Motion compensation for an electrical impedance-based positioning system will be described in greater detail in conjunction with FIG. 2. Motion compensation for a magnetic field-based positioning system will be described in greater detail in conjunction with FIG. 5. Motion compensation may also be provided for physiological (e.g., respiratory) activity, and/or may be gated for a particular point, e.g., a point in time in a cardiac cycle.

Dual-system medical device 24 is configured to be compatible with both MPS 12 and MPS 16 (i.e., is configured to cooperate with respective excitation and sensing schemes for both systems for determining position). As shown, device 24 is operatively coupled to each one of MPS 12 and MPS 16. Device 24 is particularly configured to aid registration of coordinate systems 14, 18. For this purpose, device 24 is provided with at least one "sensor-pair", where one sensor of the pair is compatible with and operatively coupled to MPS 12 while the other sensor of the pair is compatible with and operatively coupled to MPS 16. Both sensors in each sensor-pair are configured to output a respective signal to the corresponding positioning system. Such signals are thereafter used by respective systems 12, 16 to determine a respective position and orientation (P&O), expressed in its associated coordinate system. More particularly, sensors in a sensor-pair may at least be at a known distance or relationship from each other, and preferably be in such proximity to each other as to be considered to practically occupy the same physical point in three-dimensional space. As described below, respective P&O readings for each sensor of a sensor-pair are referred to herein as a fiducial pair. The recognition that each coordinate of a fiducial pair in reality refers to the same physical point in 3D space permits certain equivalences to be used in a preliminary registration of system 10 (described below in greater detail). Dual-system device 24 comprises at least one sensor-pair, and may have multiple sensor-pairs. It should be understood that device 24 may include additional electrodes and/or sensors. In particular, it can be advantageous for device 24 to include either two sensor pairs or a second sensor for at least one of the MPS systems 12, 16. In an embodiment in which two sensors in a sensor-pair are not at the same physical point in device 24, the second sensor pair or additional sensor can be used to properly orient the device for calculating the location of the fiducial pairs. Device 24 may be an electrophysiology (EP) mapping catheter, another EP catheter, or other diagnostic or treatment device.

Single-system medical device 26 is configured to be compatible with MPS 12, and, as shown, is operatively coupled to MPS 12. In this regard, device 26 includes one or more electrodes capable of sensing an electrical characteristic, which, when processed by MPS 12, outputs a P&O reading, expressed relative to coordinate system 14. In an embodiment, device 26 is configured for use in a medical procedure, mapping procedure, or other activity following the initial registration of coordinate systems 14, 18. In an embodiment, the initial registration (described below) may be valid for the duration of a particular medical session. Device 26 may be one of a plurality of medical device types, such as a non-contact EP mapping catheter that includes a plurality of electrodes. Device 26 may also be an ablation catheter, other EP catheter, or other diagnostic or treatment device.

Display 42 is configured to produce one or more images of interest such as, for example, anatomical images relating to a region of interest. Display 42 may comprise conventional apparatus known in the art.

Input/output mechanisms 44 are provided as an interface that allows a user (not shown) to interact with system 10, including various components of system 10, such as ECU 28. Input/output 44 may comprise conventional apparatus known in the art.

Image database 46 is configured to store image information relating to the patient's body, including, for example, a moving region of interest. Image database 46 may include (1) one or more two-dimensional still images acquired at respective, individual times in the past; (2) a plurality of related two-dimensional images obtained in real-time from an image acquisition device (e.g., fluoroscopic images from an x-ray imaging apparatus) wherein the image database acts as a buffer ("live" fluoroscopy); and/or (3) a sequence of related two-dimensional images defining a cine-loop (CL) wherein each image in the sequence has at least an ECG timing parameter associated therewith adequate to allow playback of the sequence in accordance with acquired real-time ECG signals obtained from an ECG monitor (not shown in FIG. 1). It should be understood that the two-dimensional images may be acquired through any imaging modality, now known or hereafter developed, for example X-ray, ultrasound, computerized tomography, nuclear magnetic resonance or the like.

ECU 28 is configured to perform a number of functions, as described in greater detail below. First, ECU 28 is responsive to at least position data from MPS 12 and MPS 16 (i.e., fiducial pairs) to determine an interpolation function that allows registration of coordinate system 14 to coordinate system 18 ("registration"). Second, ECU 28 is further configured to take a coordinate in coordinate system 14 (generated by MPS 12) and, using the interpolation function, output a corresponding coordinate in coordinate system 18 ("interpolation"). While ECU 28 may be also configured generally to perform other useful functions known in the art (e.g., process position data, interpret user input, generate display data, accurately superimpose a representation of the medical device on a pre-acquired image or sequence of images obtained from image database 46, etc.), the following description will focus on the two functions stated above, namely, registration and interpolation. To perform these functions, ECU 28 is particularly configured to include registration logic 34 and interpolation logic 36, each of which in an embodiment takes the form of programmed logic (i.e., software) stored in memory 32 and configured to be executed by processor 30. ECU 28 also includes various data structures, including reference coordinate data structure 38 and coefficient data structure 40.

Registration logic 34 is configured to establish an interpolation function to register a first, non-orthonormal coordinate system (e.g., coordinate system 14) in a second, orthonormal coordinate system (e.g., coordinate system 18). To do so, registration logic 34 may be configured to receive a set of fiducial pairs. Each fiducial pair may include a coordinate in each coordinate system, both coordinates representing the same physical point in three-dimensional (3D) space, or two points in 3D space in a predetermined, known relationship with each other (e.g., distance). The set of fiducial pairs, then, may be an N-sized set of paired respective coordinates in coordinate systems 14, 18. N may be selected as an arbitrary number of fiducial pairs large enough (and diverse enough across the region of interest) to map a relevant portion of the coordinate systems, such as a patient ROI, for example. Fiducial pair coordinates in coordinate system 14, shown as $(nX_i, nY_i, nZ_i)$, i=1, ..., N, may be received from MPS 12. Fiducial pair coordinates in coordinate system 18, shown as $(gX_i, gY_i, gZ_i)$, i=1, ..., N, may be received from MPS 16. As used herein, the prefix n refers to electrical impedance-based systems and coordinates, and the prefix g refers to magnetic field-based systems and coordinates.

Based on the received fiducial pairs, registration logic 34 may process and/or store a set of reference coordinates in data structure 38. In an embodiment, the reference coordinates stored in structure 38 are the N-sized set of n-coordinates received from MPS 12. Registration logic 34 may also be configured to define an interpolation function using an interpolation algorithm. In an embodiment, the algorithm is a thin-plate spline algorithm, which will be discussed in greater detail in conjunction with FIG. 5. Registration logic 34 is further configured to calculate coefficients 40, which are used in defining the interpolation function. The output of registration logic 34 may define a map of coordinate system 14 onto coordinate system 18. The output may be in the form of an established interpolation function, including coefficients 40 and reference coordinates 38. Alternatively, the output may be in the form of coefficients 40 and reference coordinates 38, to be used with a pre-programmed interpolation function.

Interpolation logic 36 is configured to follow the map created by registration logic 34, i.e., to apply the interpolation function to a new n-coordinate (impedance-based) in coordinate system 14 (shown as (nX, nY, nZ)) to yield a corresponding g-coordinate (shown as (gX, gY, gZ)). This data flow is shown in FIG. 1. In an embodiment, it is contemplated that logic 36 will process a real time stream of new n-coordinates to produce a corresponding real time stream of g-coordinates. Generally, interpolation logic 36 is configured (1) to apply a pre-programmed interpolation function, which makes use of reference coordinates 38 and coefficients 40, or (2) to apply an interpolation function established entirely by registration logic 34. In an embodiment, the interpolation function may be based on the same thin-plate spline algorithm applied by registration logic 34, recognizing that unknowns such as coefficients will be defined when interpolation logic 36 uses the algorithm.

In operation, system 10 may be used to register coordinate system 14 in coordinate system 18 in a preliminary, registration phase of an EP or other medical procedure. As noted above, the registration step may be based on an assessment of a plurality of measured fiducial pairs, and the equivalence that the same physical point represents in the respective coordinate systems 14, 18. MPS 12 and MPS 16 are configured to collect fiducial pairs using dual-system device 24. In this regard, ECU 28 may be configured to synchronize and/or control the collection of position data from each of MPS 12 and MPS 16. Thereafter, the collected fiducial pairs are provided to registration logic 34, which applies an interpolation algorithm. While described in much greater detail below, the interpolation algorithm involves defining a plurality of equations with a plurality of unknowns, and then solving for the unknowns. The collected fiducial pairs provide some of the information involved in solving for the unknowns. Various terms specified in the equations include corresponding coefficients, and the values determined for these coefficients (i.e., in solving the set of equations) are reflected in the data structure 40. The collected fiducial pairs also may comprise a set of reference coordinates, reflected in data structure 38. In an embodiment, this completes the registration phase.

In real-time—i.e., during a treatment or other phase following the registration phase—interpolation logic 36 may continuously accept coordinates from MPS 12. The coordinates may be derived from single-system device 26, dual-system device 24, or another medical device compatible with MPS 12 (electrical impedance-based). As described above, interpolation logic 36 is configured to apply the interpolation function (which uses reference coordinates 38 and coefficients 40) to each received coordinate in coordinate system 14 and output a corresponding coordinate in coordinate system 18. As a result, system 10 may effectively operate MPS 12 in coordinate system 18 in real-time. System 10 thus takes advantage of the ability of MPS 12 to determine the position of multiple electrodes on multiple devices simultaneously and at the same time benefits from the orthonormality and patient-independence of coordinate system 18. For example, position data collected in coordinate system 14 for purposes of generating a geometrical model or surface map of anatomical features will be shown with improved correspondence to actual images of the same anatomical features (i.e., without distortion). During real-time operation, MPS 16 may be removed from system 10, disabled, or not used, or may continue to be used to acquire position data.

Figure 2:
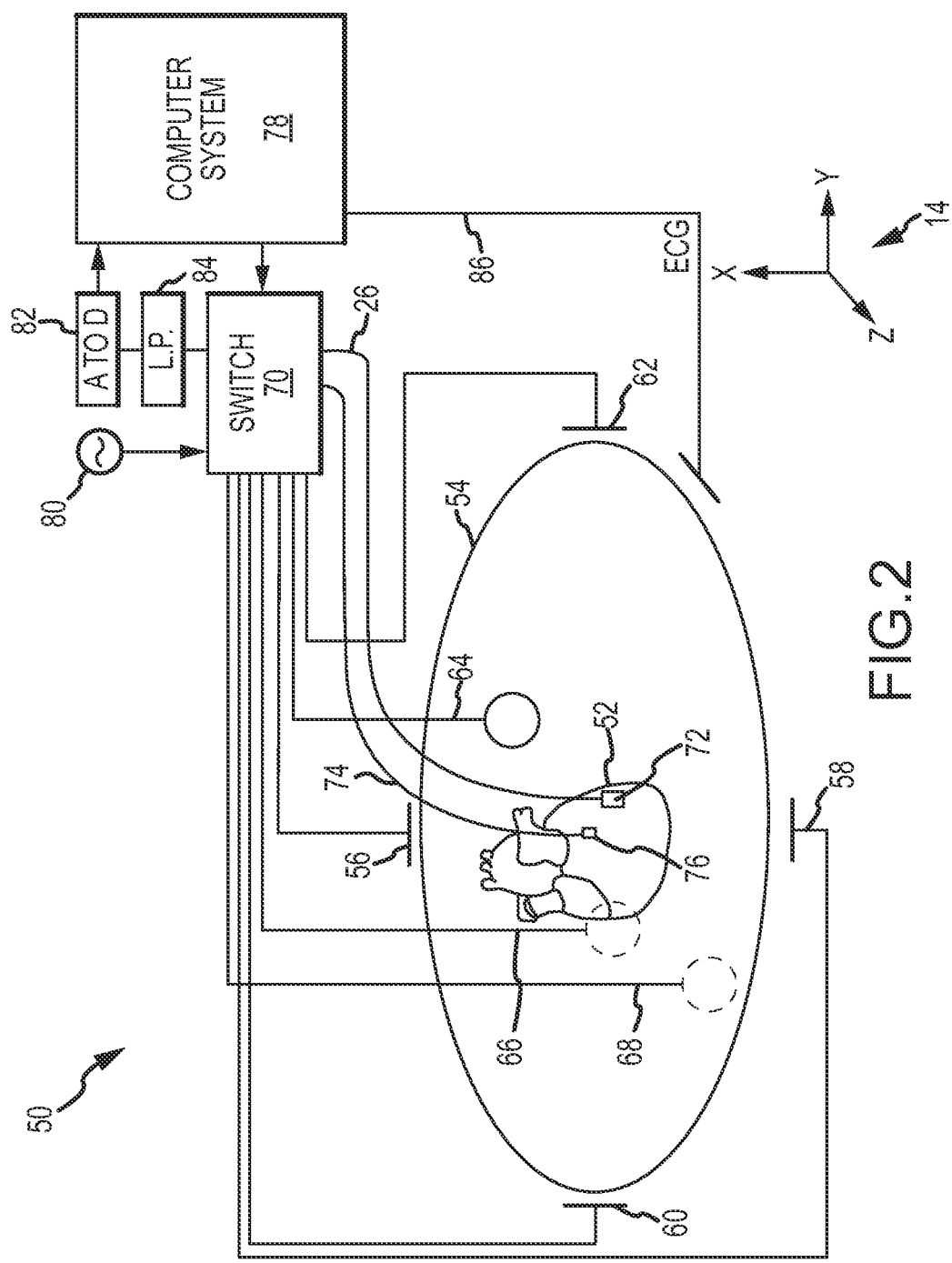
FIG. 2 is a diagrammatic and block diagram view showing, in an embodiment, an exemplary electrical impedance-based positioning system suitable for use in the system of FIG. 1.
Figure 3A:
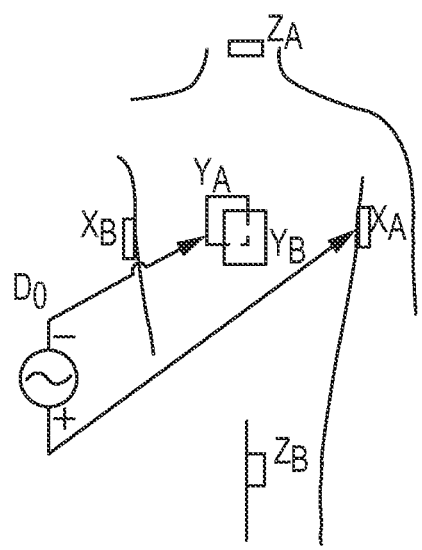
FIGS. 3A-3D are schematic diagrams of exemplary dipole pairs of driven body surface electrodes suitable for use in the embodiment of FIG. 2.
Figure 3B:
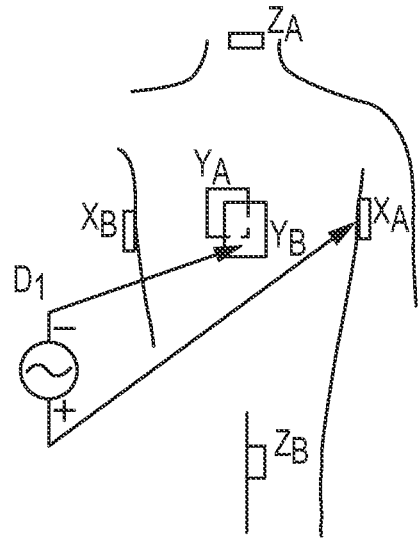
Figure 3C:
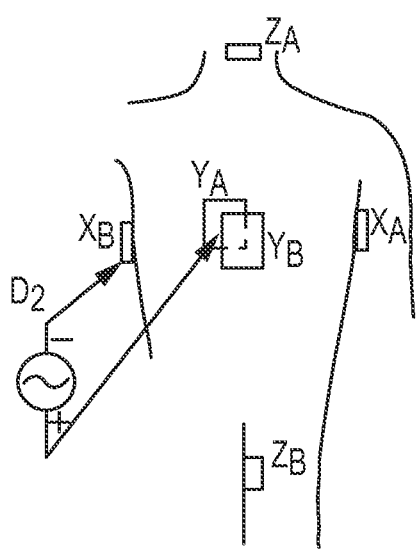
Figure 3D:
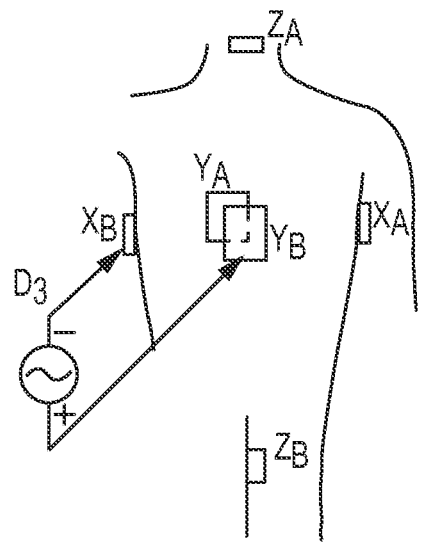

Electrical Impedance-Based MPS. FIG. 2 is a diagrammatic overview of an exemplary electrical impedance-based embodiment of MPS 12, designated system 50 (i.e., which can be used in system 10—FIG. 1). System 50 may comprise various visualization, mapping and navigation components as known in the art, including, for example, an EnSite™ Electro Anatomical Mapping System commercially available from St. Jude Medical, Inc., or as seen generally by reference to U.S. Pat. No. 7,263,397 entitled "Method and Apparatus for Catheter Navigation and Location and Mapping in the Heart" to Hauck et al., or U.S. Patent Publication No. 2007/0060833 A1 to Hauck entitled "Method of Scaling Navigation Signals to Account for Impedance Drift in Tissue", both owned by the common assignee of the present invention, and both hereby incorporated by reference in their entireties.

System 50 includes a diagrammatic depiction of a heart 52 of a patient 54. The system includes the ability to determine a catheter electrode location (i.e., position and orientation) as the catheter distal end is moved around and within a chamber of the heart 52. For this purpose, three sets of body surface electrodes (patches) are shown: (1) electrodes 56, 58 (X-axis); (2) electrodes 60, 62 (Y-axis); and (3) electrodes 64, 66 (Z-axis). Additionally, a body surface electrode ("belly patch") 68 is shown diagrammatically. The surface electrodes are all connected to a switch 70. Of course, other surface electrode configurations and combinations are suitable for use with the present invention, including fewer electrodes, e.g., three electrodes, more electrodes, e.g., twelve, or different physical arrangements, e.g., linear arrangement instead of an orthogonal arrangement.

Device 26 is also shown as a catheter with a distal electrode 72. Catheter 26 may have additional electrodes in addition to electrode 72 (e.g., a catheter tip electrode and/or ring electrodes). FIG. 2 also shows a second, independent catheter 74 with a fixed reference electrode 76, which may be stationary on the heart for calibration purposes. In many instances, a coronary sinus electrode or other fixed reference electrode 76 in the heart 52 can be used as a reference for measuring voltages and displacements.

It should be understood that catheter 26 may include still other electrodes, and in other embodiments, such as in EP or RF ablation embodiments, the other electrodes may be used for any number of diagnostic and/or therapeutic purposes. For instance, such electrodes and therefore such catheters may be used for performing ablation procedures, cardiac mapping, electrophysiological (EP) studies and other diagnostic and/or therapeutic procedures. Embodiments are not limited to any one type of catheter or catheter-based system or procedure.

FIG. 2 further shows a computer system 78, a signal generator 80, an analog-to-digital converter 82 and a low-pass filter 84. Computer system 78 includes a processing apparatus configured to perform many of the functions and operations described herein. Computer system 78 may be configured to control signal generator 80 in accordance with predetermined strategies to selectively energize various pairs (dipoles) of surface electrodes, as described in greater detail below. In operation, computer system 78 may (1) obtain raw patch data (i.e., voltage readings) via filter 84 and A-to-D converter 82 and (2) use the raw patch data (in conjunction with electrode measurements) to determine the raw, uncompensated, electrode location coordinates of a catheter electrode positioned inside the heart or chamber thereof (e.g., such as electrode 72) in three-dimensional coordinate system 14. Computer system 78 may be further configured to perform one or more compensation and adjustment functions, and to output a location in coordinate system 14 of one or more electrodes such as electrode 72. Motion compensation may include, for example, compensation for respiration-induced patient body movement, as described in U.S. patent application Ser. No. 12/980,515, entitled "Dynamic Adaptive Respiration Compensation With Automatic Gain Control", which is hereby incorporated by reference in its entirety.

In an embodiment, most or all of the conventional twelve (12) ECG leads, coupled to body surface electrodes and designated collectively by reference numeral 86, may be provided to support the acquisition of an electro-cardiogram (ECG) of the patient 54. As shown, ECG leads 86 (if provided) may be coupled directly to computer system 78 for acquisition and subsequent processing to obtain the phase of the heart in the cardiac cycle. ECG leads 86 may be also be provided to other systems.

Each body surface (patch) electrode is independently coupled to switch 70 and pairs of electrodes are selected by software running on computer system 78, which couples the patches to signal generator 80. A pair of electrodes, for example the Z-axis electrodes 64 and 66, may be excited by signal generator 80 to generate an electrical field in the body of patient 54 and heart 52. In one embodiment, this electrode excitation process occurs rapidly and sequentially as different sets of patch electrodes are selected and one or more of the unexcited (in an embodiment) surface electrodes are used to measure voltages. During the delivery of the excitation signal (e.g., current pulse), the remaining (unexcited) patch electrodes may be referenced to the belly patch 68 and the voltages impressed on these remaining electrodes are measured by the A-to-D converter 82. In this fashion, the surface patch electrodes are divided into driven and non-driven electrode sets. Low pass filter 84 may process the voltage measurements. The filtered voltage measurements are transformed to digital data by analog to digital converter 82 and transmitted to computer 78 for storage under the direction of software. This collection of voltage measurements is referred to herein as the "patch data." The software has access to each individual voltage measurement made at each surface electrode during each excitation of each pair of surface electrodes.

The patch data is used, along with measurements made at electrode 72, to determine a relative location of electrode 72 in coordinate system 14. Potentials across each of the six orthogonal surface electrodes may be acquired for all samples except when a particular surface electrode pair is driven (in an embodiment). In one embodiment, sampling while a surface electrode acts as a source or sink in a driven pair is normally avoided as the potential measured at a driven electrode during this time may be skewed by the electrode impedance and the effects of high local current density. In an alternate embodiment, however, sampling may occur at all patches (even those being driven).

Generally, in one embodiment, three nominally orthogonal electric fields are generated by a series of driven and sensed electric dipoles in order to realize localization function of the catheter in a biological conductor. Alternately, these orthogonal fields can be decomposed and any pair of surface electrodes (e.g., non-orthogonal) may be driven as dipoles to provide effective electrode triangulation.

FIGS. 3A-3D show a plurality of exemplary non-orthogonal dipoles, designated $D_0$, $D_1$, $D_2$ and $D_3$, set in coordinate system 14. In FIGS. 3A-3D, the X-axis surface electrodes are designated $X_A$ and $X_B$, the Y-axis surface electrodes are designated $Y_A$ and $Y_B$, and the Z-axis electrodes are designated $Z_A$ and $Z_B$. For any desired axis, the potentials measured across an intra-cardiac electrode 72 resulting from a predetermined set of drive (source-sink) configurations may be combined algebraically to yield the same effective potential as would be obtained by simply driving a uniform current along the orthogonal axes. Any two of the surface electrodes 56, 58, 60, 62, 64, 66 (see FIG. 2) may be selected as a dipole source and drain with respect to a ground reference, e.g., belly patch 68, while the unexcited body surface electrodes measure voltage with respect to the ground reference. The measurement electrode 72 placed in heart 52 is also exposed to the field from a current pulse and is measured with respect to ground, e.g., belly patch 68. In practice, a catheter or multiple catheters within the heart may contain multiple electrodes and each electrode potential may be measured separately. As previously noted, alternatively, at least one electrode may be fixed to the interior surface of the heart to form a fixed reference electrode 76, which may also be measured with respect to ground.

Data sets from each of the surface electrodes and the internal electrodes are all used to determine the location of measurement electrode 72 within heart 52. After the voltage measurements are made, a different pair of surface electrodes is excited by the current source and the voltage measurement process of the remaining patch electrodes and internal electrodes takes place. The sequence occurs rapidly, e.g., on the order of 100 times per second in an embodiment. To a first approximation the voltage on the electrodes within the heart bears a linear relationship with position between the patch electrodes that establish the field within the heart, as more fully described in U.S. Pat. No. 7,263,397 referred to above.

In summary, FIG. 2 shows an exemplary system that employs seven body surface electrodes (patches), which may be used for injecting current and sensing resultant voltages. Current may be driven between two patches at any time. Measurements may be performed between a non-driven patch and, for example, belly patch 68 as a ground reference. A patch bio-impedance, also referred to as a "patch impedance" may be computed according to the following equation:

$$BioZ[n \to m][k] = \frac{V_k}{I_{n \to m}}$$

where $V_k$ is the voltage measured on patch k and $I_{n \to m}$ is a known constant current driven between patches n and m. The position of an electrode may be determined by driving current between different sets of patches and measuring one or more patch impedances. In one embodiment, time division multiplexing may be used to drive and measure all quantities of interest. Position determining procedures are described in more detail in U.S. Pat. No. 7,263,397 and Publication 2007/0060833 referred to above, as well as other references.

As stated in the Background, because electrical impedance-based systems depend on electrical current flow in the human body, their coordinate systems (i.e., the electrical fields produced in the human body) can be non-homogenous, anisotropic, and not orthonormal. System 50 may include features to account for such electrical field inconsistencies, such as correction of inhomogenous electrical fields, as described in U.S. Patent Application Publication 2008/0221643, entitled "System and Method for Correction of Inhomogenous Fields", which is hereby incorporated by reference in its entirety.

Figure 4:
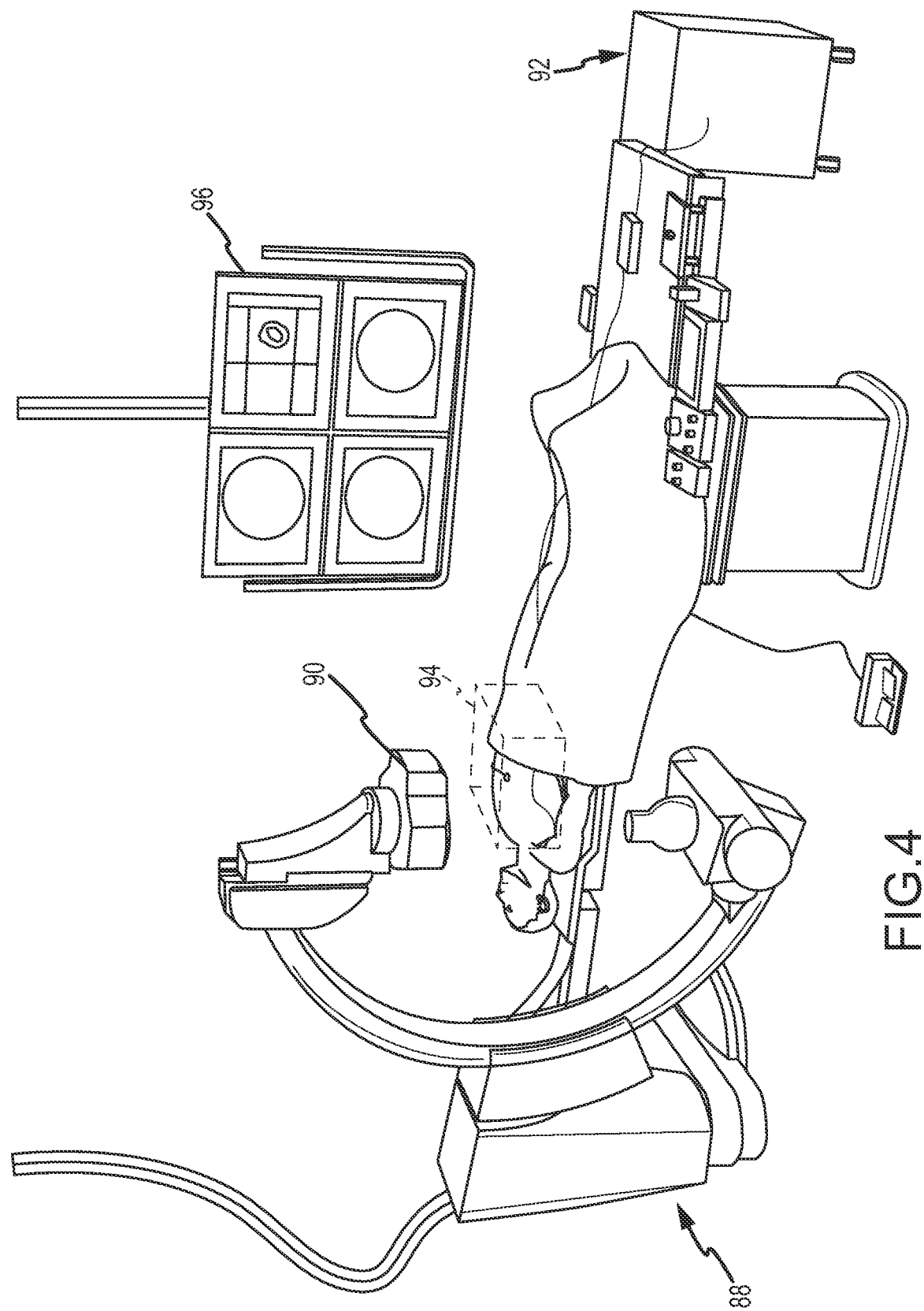
FIG. 4 is a diagrammatic view showing, in an embodiment, an exemplary magnetic field-based positioning system suitable for use in the system of FIG. 1.

Magnetic Field-Based MPS. FIG. 4 is a diagrammatic view of an exemplary magnetic field-based embodiment of MPS 16 in a fluoroscopy-based imaging environment, designated system 88. The system 88 includes a magnetic transmitter assembly (MTA) 90 and a magnetic processing core 92 for determining position and orientation (P&O) readings. The MTA 90 is configured to generate the magnetic field(s) in and around the patient's chest cavity in a predefined three-dimensional space designated as motion box 94 in FIG. 4. Magnetic field sensors coupled with dual-system device 24 or another medical device are configured to sense one or more characteristics of the magnetic field(s) and, when the sensors are in the motion box 94, each generates a respective signal that is provided to the magnetic processing core 92. The processing core 92 is responsive to these detected signals and is configured to calculate respective three-dimensional position and orientation (P&O) readings for each magnetic field sensor in the motion box 94. Thus, the MPS system 88 enables real-time tracking of each magnetic field sensor in three-dimensional space. The position of the sensors may be shown on a display 96 relative to, for example only, a cardiac model or geometry.

Figure 5:
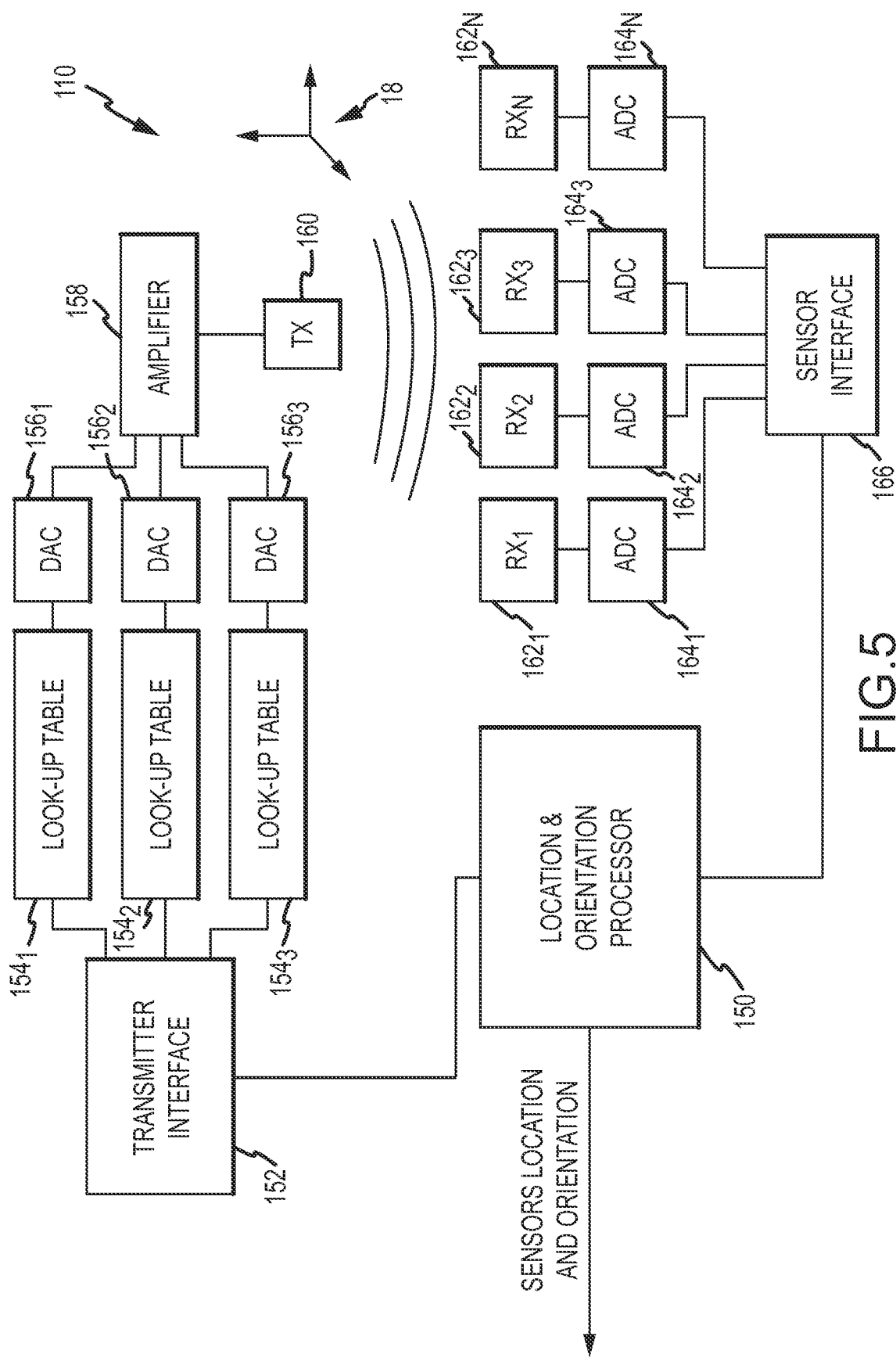
FIG. 5 is a schematic and block diagram view showing, in an embodiment, an exemplary magnetic field-based positioning system suitable for use in the system of FIG. 1.

FIG. 5 is a schematic and block diagram view of another exemplary magnetic field-based embodiment of MPS 16, designated MPS 110, as also seen by reference to U.S. Pat. No. 7,386,339, hereby incorporated by reference in its entirety, and portions of which are reproduced below. It should be understood that variations are possible, for example, as also seen by reference to U.S. Pat. Nos. 7,197,354, and 6,233,476, also hereby incorporated by reference in their entireties.

MPS system 110 includes a location and orientation processor 150, a transmitter interface 152, a plurality of look-up table units 154$_1$, 154$_2$ and 154$_3$, a plurality of digital to analog converters (DAC) 156$_1$, 156$_2$ and 156$_3$, an amplifier 158, a transmitter 160, a plurality of MPS sensors 162$_1$, 162$_2$, 162$_3$ and 162$_N$, a plurality of analog to digital converters (ADC) 164$_1$, 164$_2$, 164$_3$ and 164$_N$ and a sensor interface 166.

MPS 110 is configured to acquire positioning (localization) data (i.e., position and orientation—P&O) of MPS sensors 162. For some sensors 162, the P&O may be expressed with five degrees of freedom as a position (i.e., a coordinate in three axes X, Y and Z) and orientation (i.e., an azimuth and elevation) of the respective sensor 162 in a magnetic field relative to magnetic field transmitter 160. For other sensors 162, the P&O may be expressed with six degrees of freedom as a position (X, Y, and Z) and orientation (i.e., roll, pitch, and yaw). The P&O may be based on capturing and processing the signals received from a sensor 162 while in the presence of a controlled low-strength AC magnetic field. Accordingly, sensors 162 may each comprise one or more magnetic field detection coil(s), and it should be understood that variations as to the number of coils, their geometries, spatial relationships, the existence or absence of cores and the like are possible. From an electromagnetic perspective, all sensors are created equal: voltage is induced on a coil residing in a changing magnetic field, as contemplated here. Sensors 162 are thus configured to detect one or more characteristics of the magnetic field(s) in which they are disposed and generate an indicative signal, which is further processed to obtain the P&O thereof. For one example of a sensor, see U.S. Pat. No. 7,197,354 entitled "System for Determining the Position and Orientation of a Catheter" issued to Sobe, hereby incorporated by reference in its entirety.

Transmitter interface 152, DAC units 156, and transmitter 160 are provided to create the controlled low-strength AC magnetic field. MPS sensors 162, ADC units 164, and sensor interface 166 are provided to create signals indicative of characteristics of the field for P&O determination. Transmitter interface 152 is connected to location and orientation processor 150 and to look-up table units 154$_1$, 154$_2$ and 154$_3$. DAC units 156$_1$, 156$_2$ and 156$_3$ are connected to a respective one of look-up table units 154$_1$, 154$_2$ and 154$_3$ and to amplifier 158. Amplifier 158 is further connected to transmitter 160. Transmitter 160, also marked TX, may be coupled to a portion of the operating environment (e.g., bed or an imaging apparatus). MPS sensors 162$_1$, 162$_2$, 162$_3$ and 162$_N$ are further marked RX$_1$, RX$_2$, RX$_3$ and RX$_N$, respectively. Analog to digital converters (ADC) 164$_1$, 164$_2$, 164$_3$ and 164$_N$ are respectively connected to sensors 162$_1$, 162$_2$, 162$_3$ and 162$_N$ and to sensor interface 166. Sensor interface 166 is further connected to location and orientation processor 150.

Each of look-up table units 154$_1$, 154$_2$ and 154$_3$ produces a cyclic sequence of numbers and provides it to the respective DAC unit 156$_1$, 156$_2$ and 156$_3$, which in turn translates it to a respective analog signal. Each of the analog signals is respective of a different spatial axis. In the present example, look-up table 154$_1$ and DAC unit 156$_1$ produce a signal for the X axis, look-up table 154$_2$ and DAC unit 156$_2$ produce a signal for the Y axis and look-up table 154$_3$ and DAC unit 156$_3$ produce a signal for the Z axis.

DAC units 156$_1$, 156$_2$ and 156$_3$ provide their respective analog signals to amplifier 158, which amplifies and provides the amplified signals to transmitter 160. Transmitter 160 provides a multiple axis electromagnetic field, which can be detected by MPS sensors 162$_1$, 162$_2$, 162$_3$ and 162$_N$. Each of MPS sensors 162$_1$, 162$_2$, 162$_3$ and 162$_N$ detects an electromagnetic field, produces a respective electrical analog signal and provides it to the respective ADC unit $164_1$, $164_2$, $164_3$ and $164_N$ connected thereto. Each of the ADC units $164_1$, $164_2$, $164_3$ and $164_N$ digitizes the analog signal fed thereto, converts it to a sequence of numbers and provides it to sensor interface 166, which in turn provides it to location and orientation processor 150. Location and orientation processor 150 analyzes the received sequences of numbers, thereby determining the location and orientation of each of the MPS sensors $162_1$, $162_2$, $162_3$ and $162_N$. Location and orientation processor 150 further determines distortion events and updates look-up tables $154_1$, $154_2$ and $154_3$, accordingly. In an embodiment in which MPS 110 is implemented as a part of system 10 (e.g., as MPS 16), location and orientation processor 150 may be implemented as a part of ECU 28.

MPS 110 may compensate for respiration-induced and other patient body motion, substantially as described in U.S. patent application Ser. No. 12/650,932, entitled "Compensation of Motion in a Moving Organ Using an Internal Position Reference Sensor", hereby incorporated by reference in its entirety. One of MPS sensors 162 may be a patient reference sensor (PRS) configured to provide a stable positional reference on the patient's body for such motion compensation. The PRS may be attached to the patient's manubrium sternum or another location.

In an embodiment, MPS 110 may also include an electrocardiogram (ECG) monitor (not shown in FIG. 5) configured to continuously detect an electrical timing signal of the heart organ through the use of a plurality of ECG electrodes (not shown), which may be externally-affixed to the outside of a patient's body. The timing signal generally corresponds to the particular phase of the cardiac cycle, among other things. The ECG signal may be used for ECG synchronized playback of a previously captured sequences of images (cine loop). The ECG monitor and ECG-electrodes may comprise conventional components.

Figure 6:
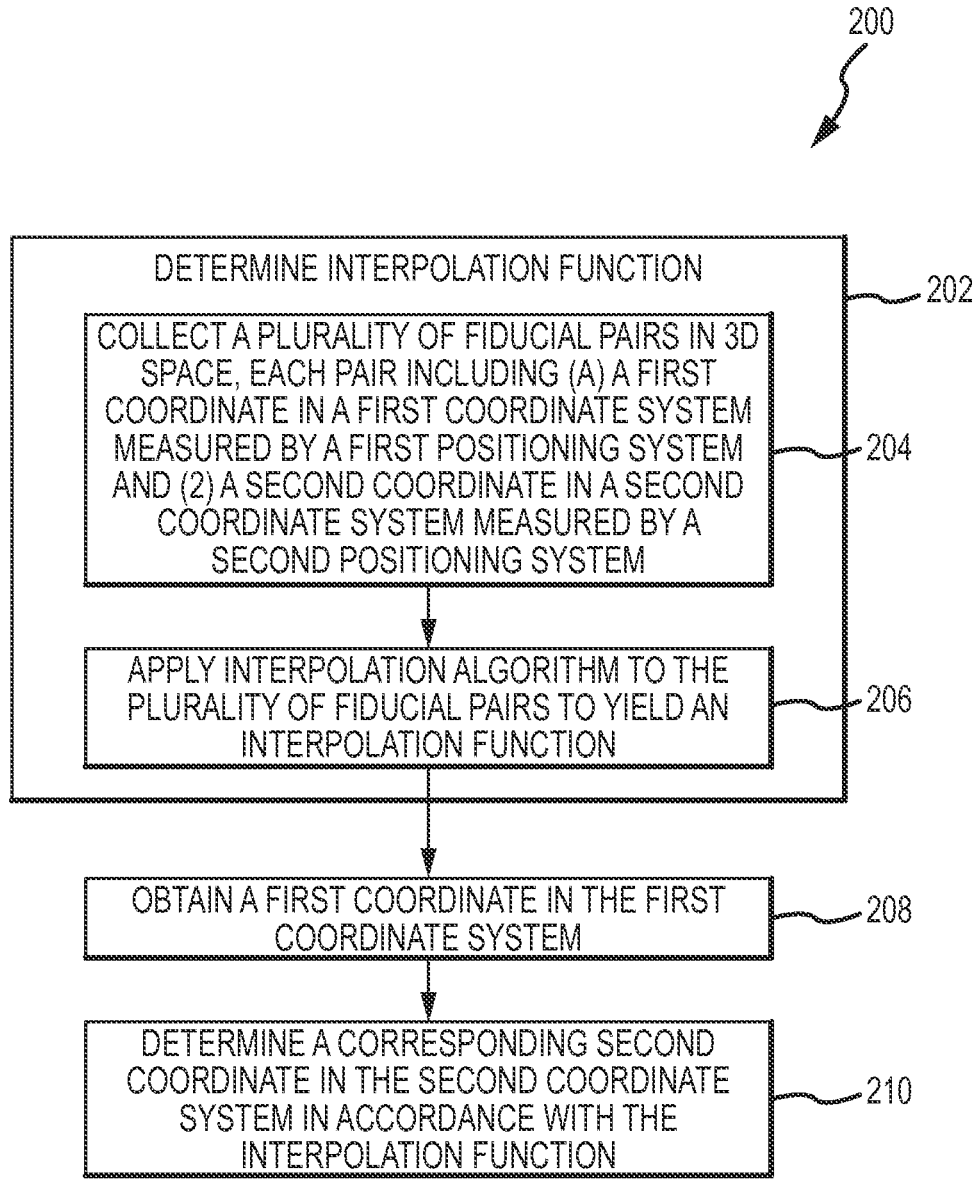
FIG. 6 is a flowchart illustrating an embodiment of a method of operating the positioning system of FIG. 1.

Combined System 10. FIG. 6 is a flowchart of a method of operating a positioning system, designated method 200. Method 200 will be described with reference to an embodiment of system 10. In the following embodiment, MPS 12 is an electrical impedance-based positioning system, and MPS 16 is a magnetic field-based positioning system. However, it should be understood that the method described herein may find use with other systems, other MPS types, and other combinations thereof. Consistent with previous portions of this disclosure, descriptions and coordinate symbols beginning with n are associated with an electrical impedance-based positioning system, whereas descriptions and coordinate symbols beginning with g are associated with a magnetic field-based positioning system.

Method 200 begins at step 202 by determining an interpolation function configured to register coordinate system 14 associated with MPS 12 in a second coordinate system 18 associated with second MPS 16. Step 202 includes two sub-steps 204, 206. The first sub-step 204 involves collecting a plurality of fiducial pairs in three-dimensional (3D) space throughout the physical 3D space (i.e., the region of interest, typically in an anatomical regional of interest in a patient). It should be understood that both coordinate systems 14, 18 are defined throughout this physical 3D space. Accordingly, each fiducial pair will include (1) a first coordinate expressed in coordinate system 14 (measured by MPS 12), represented by (nX, nY, nZ), and (2) a second coordinate expressed in coordinate system 18 (measured by MPS 16), represented by (gX, gY, gZ). Fiducial pairs may be collected using a single device (e.g., device 24) compatible with both MPS 12 and MPS 16. Collection may be performed under the direction of ECU 28. The collected fiducial pairs may cover the entire navigational domain (i.e., volume or region of interest). Coordinates in a fiducial pair may be respectively and independently compensated for patient body motion by MPS 12 and MPS 16 as described hereinabove. To ensure a smooth interpolation function, sub-step 204 may also involve discarding fiducial pairs whose coordinates correspond to a physical point that is less than a pre-determined minimum distance (e.g., 4 millimeters) from another physical point corresponding to a previously-collected fiducial pair. Degenerate pairs (i.e., two different n-coordinates for a single g-coordinate, or vice-versa) may also be discarded. For the interpolation function to be unambiguous, collected fiducial pairs must not all lie in the same plane (i.e., the fiducial pairs must represent physical points in the region of interest that span all three dimensions).

Second sub-step 206 involves applying an interpolation algorithm to the collected plurality of fiducial pairs to yield a defined interpolation function. Sub-step 206 can also be considered a registration step in which the n coordinate system 14 is registered in the g coordinate system 18. In an embodiment, the interpolation algorithm used is the thin plate spline algorithm ("the algorithm"), but other interpolation algorithms may find use with method 200 and system 10. The following description of the thin plate spline algorithm uses basis function r, though other basis functions may be used and remain within the scope and spirit of the present invention. Furthermore, the algorithm as described herein is directed to the registration of an inhomogenous, non-orthonormal electrical impedance-based coordinate system with a generally orthonormal magnetic field-based coordinate system, but other coordinate system type registrations may be performed with the algorithm and/or with method 200.

ECU 28 (e.g., via registration logic 34) is configured to perform the processing functions in sub-steps 204, 206.

The algorithm accepts the fiducial pairs collected in sub-step 204 as an input, wherein each fiducial pair has the following two coordinates:

$$(nX_i, nY_i, nZ_i)$$

and $$(gX_i, gY_i, gZ_i)$$

Where the subscript index i=1, . . . , N is the index numbering the fiducial pairs and N is the total number of non-discarded fiducial pairs collected in sub-step 204. In an embodiment, about 200 fiducial pairs may well describe a geometry and also allow a defined interpolation function to operate robustly in real time, so N may be about 200. Variation to the number of fiducial pairs is possible, as will be appreciated by those of ordinary skill in the art.

The goal of the interpolation algorithm is to compute a continuous map relating the entire n-coordinate system 14 to the entire g-coordinate system 18. In the thin plate spline algorithm, the map can be represented by a function in each dimension that relates a point (nX, nY, nZ) in n-space to a point (gX, gY, gZ) in g-space as set forth in the set of equations (1) below:

$$gX(nX, nY, nZ) = b_1^x nX + b_2^x nY + b_3^x nZ + c^x + \sum_{j=1}^{N} a_j^x \Psi_j(\overrightarrow{nX}) \quad (1)$$

$$gY(nX, nY, nZ) = b_1^y nX + b_2^y nY + b_3^y nZ + c^y + \sum_{j=1}^{N} a_j^y \Psi_j(n\vec{X})$$

$$gZ(nX, nY, nZ) = b_1^z nX + b_2^z nY + b_3^z nZ + c^z + \sum_{j=1}^{N} a_j^z \Psi_j(n\vec{X})$$

where $a_j^x$, $a_j^y$, $a_j^z$, $b_k^x$, $b_k^y$, $b_k^z$, and $c^x$, $c^y$, $c^z$, $j=1,\ldots,N$, $k=1, 2, 3$, are (initially-unknown) coefficients (e.g., coefficients 40) for which respective values must be determined, $n\vec{X}$ is the three-dimensional point (nX, nY, nZ), and $\Psi_j(n\vec{X})$ is a three-dimensional basis function. The basis function may be selected from a range of the radial basis functions. The exact form of the basis function may be defined according to the dimensionality of the spline (the spline is three-dimensional for the algorithm described herein). One set of radial basis functions that may be used is the Euclidean distance as set forth in equation (2) below:

$$\Psi_j(n\vec{X}) = \sqrt{(nX-x_j)^2 + (nY-y_j)^2 + (nZ-z_j)^2} \quad (2)$$

which may be expressed in short form as in equation (3) below:

$$\Psi_j(n\vec{X}) = |n\vec{X} - n\vec{X}_j| \quad (3)$$

Solving for the unknown coefficients may include a smoothing parameter $\lambda$, which controls how close the mapped solution $g(nX_i, nY_i, nZ_i)$ is to the measured point $(gX_i, gY_i, gZ_i)$. In other words, smoothing parameter $\lambda$ determines the amount by which a g-coordinate output by the interpolation function based on an particular n-coordinate input can differ from a measured g-coordinate in a fiducial pair with the particular n-coordinate. If $\lambda$ is set to zero, the mapped solution (i.e., interpolation function output) for each measured n-coordinate is equal to the measured g-coordinate in a fiducial pair with that n-coordinate, such that $g(nX_i, nY_i, nZ_i) = (gX_i, gY_i, gZ_i)$ for all $(nX_i, nY_i, nZ_i)$. A non-zero $\lambda$ results in a smoother solution by avoiding over-fitting noisy measurements in the fiducial pairs. The value of $\lambda$ may vary from registration to registration and/or from system to system. In general, $\lambda$ may be a number greater than zero determined through routine experimentation to strike a proper balance between accurately reflecting measured fiducial pairs and avoiding over-fitting noisy measurements. $\lambda$ may have a value relative to the number of fiducial pairs. For example, in an embodiment, $\lambda$ may be assigned the value 0.025N, where N is the number of fiducial pairs (e.g., such that $\lambda=5$ for N=200). Implementing $\lambda$ and setting equations (1) in an iterative form to solve for the 3N+12 coefficients results in the following set of equations (4):

$$gX_i = b_1^x nX_i + b_2^x nY_i + b_3^x nZ_i + c^x + \sum_{j=1}^{N} a_j^x (\Psi_j(n\vec{X}_i) - \lambda \delta_{ij}) \quad (4)$$

$$gY_i = b_1^y nX_i + b_2^y nY_i + b_3^y nZ_i + c^y + \sum_{j=1}^{N} a_j^y (\Psi_j(n\vec{X}_i) - \lambda \delta_{ij})$$

$$gZ_i = b_1^z nX_i + b_2^z nY_i + b_3^z nZ_i + c^z + \sum_{j=1}^{N} a_j^z (\Psi_j(n\vec{X}_i) - \lambda \delta_{ij})$$

$$\sum_{j=1}^{N} a_j^m = 0, \sum_{j=1}^{N} a_j^m nX_j = 0, \sum_{j=1}^{N} a_j^m nY_j = 0, \sum_{j=1}^{N} a_j^m nZ_j = 0, \quad (5)$$

$$m = x, y, z$$

where $\delta_{ij}$ are the Kronecker symbols defined by the following equations:

$$\delta_{ij} = 1 \quad i=j$$

$$\delta_{ij} = 0 \quad i \neq j$$

The equation set (4) is a set of 3N+12 equations that includes 3N+12 unknowns. Equations (4) and (5) can be solved (e.g., by registration logic 34) to find the 3N+12 unknown coefficients for equation set (1), whose values may be stored as coefficients 40. To solve equations (4) and (5), the collected fiducial pairs are used. Note that the equation set (4) needs data to solve for the unknown coefficients: $(gX_i, gY_i, gZ_i)$ and $n\vec{X}_i = (nX_i, nY_i, nZ_i)$. The fiducial pairs provide this data: recall that each fiducial pair has components $(nX_i, nY_i, nZ_i)$ and $(gX_i, gY_i, gZ_i)$, where the subscript index $i=1, \ldots, N$ is the index numbering the fiducial pairs and N is the total number of non-discarded fiducial pairs collected in sub-step 204. Thus, at sub-step 206, the fiducial pair g-coordinates are used on the left-hand side of equations (4). The fiducial pair n-coordinates are used throughout the right-hand side of equations (4), including in the summation term, as well as for equations (5). The art is replete for approaches (e.g., software-based) to solve a number of equations with the same number of unknowns, and accordingly, conventional approaches may be used to determine the respective values for the unknown coefficients.

As described above, the collected fiducial pairs are used to solve for the unknown coefficients in equations (4) so that those coefficients may be applied in equations (1)—that is the first purpose of the fiducial pairs. The fiducial pairs—or, more accurately, the electrical impedance-based coordinates in the fiducial pairs—also have a distinct second purpose: continuous use in real-time application of equations (1), as will be described below. Accordingly, the n-coordinates in the fiducial pairs (i.e., the coordinates measured in sub-step 204 by electrical impedance-based MPS 12) are stored in reference coordinates data structure 38 for use in the summation portion of equations (1) in real-time operation.

Equation set (1), now defined by virtue of known values for coefficients 40 and further by virtue of a populated set of reference coordinates 38 (e.g., the n-coordinates taken from the fiducial pairs), represent the output of sub-step 206 (and of step 202), namely, the interpolation function g(nX, nY, nZ).

After the interpolation function is determined, it may be applied (e.g., by interpolation logic 36) during real-time device usage (e.g., navigation, data collection, etc.) according to steps 208, 210. Step 208 involves obtaining a real-time coordinate in coordinate system 14 with MPS 12 (shown as (nX, nY, nZ) in equation set (1)). The real-time coordinate may be motion compensated by MPS 12. Step 210 involves determining a corresponding real-time coordinate in coordinate system 18 ((gX, gY, gZ)) in accordance with the interpolation function (e.g., by interpolation logic 36). If the interpolation function is a result of the thin-plate spline algorithm discussed herein, applying the interpolation function requires a plurality of reference coordinates in coordinate system 14, such as reference coordinates 38, as input for the basis functions in the summation term in equations (1). As can be seen from the summation term of equations (1), the interpolation function in each dimension requires the same number of reference coordinates, N, as were used by the algorithm to establish the function (i.e., solve for the coefficients). Accordingly, step 210 may involve the recall of an N-sized set of reference coordinates 38 to apply the interpolation function. As noted above, the reference coordinates may be the n-coordinates (i.e., the electrical impedance-based coordinates from the fiducial pairs) collected in sub-step 204. Each of the N reference coordinates (i.e., each non-discarded electrical impedance-based coordinate collected in sub-step 204) is used by the summation term of equations (1), in each dimension, to relate each new real-time n-coordinate into g-space.

Steps 208, 210 may be continuously repeated with respect to position data from multiple electrical impedance-based sensors on multiple medical devices from MPS 12. By repeating steps 208, 210, MPS 12 may be operated in coordinate system 18 substantially in real time.

The steps of method 200 may be temporally distributed among different phases of a medical procedure. Step 202 (including sub-steps 204, 206) may be performed during a preliminary, registration phase. Steps 208, 210 may be performed during a subsequent treatment or other phase, for example. In other words, sub-steps 204, 206 may be considered non-real-time relative to the treatment or other procedure, while steps 208, 210 may be performed substantially in real-time during the treatment or other procedure.

Operating a positioning system according to method 200 presents many advantages. As stated in the Background, the coordinate system of an electrical impedance-based MPS may be inhomogenous, anisotropic, and not orthonormal. These characteristics can result in distorted geometries, for example. However, an electrical impedance-based MPS generally provides the ability to track a relatively large number of sensors on several devices at the same time. In contrast, while the coordinate system of a magnetic field-based MPS is generally orthonormal and homogenous, such a magnetic-field based MPS may be limited to tracking a relatively smaller number of sensors. By enabling registration of the coordinate system of an electrical impedance-based MPS in the coordinate system of a magnetic field-based MPS, method 200 provides the advantages of both types of positioning system while minimizing the drawbacks—a relatively large number of sensors can be tracked on multiple devices in an orthonormal, homogenous coordinate system.

It should be understood that an electronic controller or ECU as described above for certain embodiments may include conventional processing apparatus known in the art, capable of executing pre-programmed instructions stored in an associated memory, all performing in accordance with the functionality described herein. To the extent that the methods described herein are embodied in software, the resulting software may be stored in an associated memory and where so described, may also constitute the means for performing such methods. Implementation of certain embodiments of the invention, where done so in software, would require no more than routine application of programming skills by one of ordinary skill in the art, in view of the foregoing enabling description. Such an electronic controller or ECU may further be of the type having both ROM, RAM, a combination of non-volatile and volatile (modifiable) memory so that the software can be stored and yet allow storage and processing of dynamically produced data and/or signals.

The systems and methods described herein may be tested to ensure the accuracy of the registration process and of the resulting interpolation function. For example, a medical device having multiple sensors (e.g., electrodes) with a known physical relationship with each other (i.e., known distances between sensors) can be coupled to an MPS having a non-orthonormal coordinate system. Distances between sensors can be obtained from, e.g., the medical device product catalog. Position readings from the multiple sensors can be input to the interpolation function, and the distances between respective orthonormal coordinate system outputs can be compared to the known distances between electrodes (e.g., by logic executed by ECU 28). Additionally or alternatively, a medical device having similar sensor characteristics as the device used to collect the fiducial pairs (i.e., a second dual system medical device) may be swept through the mapped space to ensure that the same results are obtained.

The coordinate system registration and resulting interpolation function described herein may be updated during a medical procedure to ensure continued accuracy of the interpolation function. For example, an electrical impedance-based coordinate system may drift during a medical procedure due to changes in the biological impedance of the patient. Such a biological impedance change may result from, e.g., changes in cell chemistry due to saline or other hydration drips, dehydration, or changes in body temperature. To counteract impedance drift, steps 202 (including sub-steps 204, 206) may be repeated—i.e., a new set of fiducial pairs may be collected and the interpolation function may be re-determined—to update the registration between the electrical impedance-based coordinate system and the magnetic field-based coordinate system.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the invention as defined in the appended claims.

What is claimed is:

1. A method of operating a computer system for locating a medical device within a body, the computer system comprising an electrical-based positioning system and a magnetic-based positioning system, the method comprising the steps of:

determining, by an electronic control unit (ECU) comprising a processor, an interpolation function configured to register a first, non-orthonormal coordinate system of the electrical-based positioning system in a second, orthonormal coordinate system of the magnetic-based positioning system, wherein said first and second coordinate systems are independent, wherein said determining an interpolation function comprises:

receiving a first signal from the electrical-based positioning system for tracking a location of an electrode coupled to the medical device;

receiving a second signal from the magnetic-based positioning system for tracking a location of a magnetic sensor coupled to the medical device;

collecting, by the ECU based on the second signal, a plurality of fiducial pairs in three-dimensional (3D) space distributed throughout a region of interest, each fiducial pair including (1) a first coordinate in said first coordinate system measured by the electrical-based positioning system and (2) a second coordinate in said second coordinate system measured by the magnetic-based positioning system, each fiducial pair corresponding to a physical point in 3D space in the region of interest based on the second signal;

discarding any fiducial pairs that are degenerate; and applying, by the ECU, an interpolation algorithm to said plurality of fiducial pairs to yield said interpolation function, wherein the interpolation algorithm determines one or more coefficients for modifying coordinates of the plurality of fiducial pairs;

obtaining, by the ECU, a first coordinate in said first coordinate system within said region of interest;

determining, by the ECU, a corresponding second coordinate in said second coordinate system in accordance with said interpolation function and the one or more coefficients; and displaying a location of the medical device based on the second coordinate, determined in accordance with said interpolation function, for each of the plurality of fiducial pairs.

2. The method of claim 1, wherein said interpolation algorithm is a thin-plate spline algorithm.

3. The method of claim 2, wherein said thin-plate spline algorithm includes Euclidean distance basis functions.

4. The method of claim 2, wherein said thin-plate spline algorithm includes a smoothing parameter corresponding to a nonzero amount by which the second coordinate determined in accordance with said interpolation function corresponding to the obtained first coordinate can differ from the measured second coordinate in a fiducial pair with the measured first coordinate that is equivalent to said obtained first coordinate.

5. The method of claim 1, wherein said collecting step includes discarding a fiducial pair when a distance to a nearest fiducial point is less than a pre-determined minimum distance.

6. The method of claim 5, wherein said pre-determined minimum distance is at least 4 millimeters.

7. The method of claim 1, wherein said first coordinate is compensated for patient body movement.

8. The method of claim 1, wherein said obtaining step includes compensating for patient body movement in said first non-orthonormal coordinate system.

9. A method of relating a real-time first coordinate in a first coordinate system of an electrical-based positioning system into a second coordinate system of a magnetic-based positioning system for locating a medical device within a body, comprising:

establishing an interpolation function configured to receive as input said real-time first coordinate from a first electrode electrically coupled with the electrical-based positioning system for tracking a location of the first electrode coupled to the medical device and to output a second coordinate from the magnetic-based positioning system for tracking a location of a first magnetic sensor coupled to the medical device in said second coordinate system, wherein the electrical-based positioning system and the magnetic-based positioning system are independent, said establishing step comprising:

collecting a plurality of fiducial pairs in three-dimensional (3D) space, each fiducial pair including (1) a non-real-time first coordinate in said first coordinate system and (2) a non-real-time second coordinate in said second coordinate system, discarding any fiducial pairs that are degenerate, and applying an interpolation algorithm to said plurality of fiducial pairs to yield said interpolation function, wherein said fiducial pairs are input to said interpolation algorithm and wherein said interpolation algorithm determines one or more coefficients for modifying coordinates of said plurality of fiducial pairs, and wherein the interpolation algorithm uses a smoothing parameter that corresponds to an amount by which the second coordinate, determined in accordance with said interpolation function corresponds to an obtained first coordinate, differs from a measured second coordinate in a fiducial pair with a measured first coordinate that is equivalent to the obtained first coordinate;

applying said interpolation function to said real-time first coordinate, by a computer processor associated with a positioning system, to relate said real-time first coordinate into said second coordinate system; and displaying a location of the medical device based on the second coordinate, determined in accordance with said interpolation function, for each of the plurality of fiducial pairs.

10. The method of claim 9, wherein said interpolation algorithm is a thin-plate spline algorithm.

11. The method of claim 9, wherein said thin-plate spline algorithm includes a nonzero smoothing parameter.

* * * * *